United States Patent [19]

Rozzell

[11] Patent Number: 4,880,738

[45] Date of Patent: Nov. 14, 1989

[54] PRODUCTION OF AMINO ACIDS USING COUPLED ENZYME SYSTEMS

[75] Inventor: J. David Rozzell, Cambridge, Mass.

[73] Assignee: Genetics Institute, Inc., Cambridge, Mass.

[21] Appl. No.: 873,920

[22] Filed: Jun. 13, 1986

[51] Int. Cl.$^4$ .................. C12P 13/04; C12P 13/22
[52] U.S. Cl. .................................. 435/106; 435/107; 435/108; 435/109; 435/110; 435/113; 435/114; 435/115; 435/116; 435/175
[58] Field of Search .............. 435/42, 106, 107, 108, 435/109, 110, 113, 114, 115, 116, 175, 176, 177, 183, 227, 191, 180, 232; 260/377

[56] References Cited

U.S. PATENT DOCUMENTS

| 3,183,170 | 5/1965 | Kitai et al. | 435/116 |
| 4,013,508 | 3/1977 | Zangrandi et al. | 435/109 |
| 4,318,980 | 3/1982 | Boguslaski et al. | 435/7 |
| 4,416,992 | 11/1983 | Arera et al. | 435/174 |
| 4,518,692 | 5/1985 | Rozzell | 435/116 |

FOREIGN PATENT DOCUMENTS 8701727  3/1987  PCT Int'l Appl. ................ 435/106

OTHER PUBLICATIONS

Allen, "Lactate-Oxaloacetate Transhydrogenase from Veillonella Alcalescens", Methods in Enzymology, vol. 89, 367–376, 1982.

Rozzell et al., "Combining Enzymatic and Chemical Steps in the Synthesis of Biochemically Valuable Compounds: Isotopically Chiral Methyl Acetate", J. Org. Chem., vol. 48, 1190–1193, 1983.

Primary Examiner—Charles F. Warren
Assistant Examiner—Gail Knox
Attorney, Agent, or Firm—David L. Berstein; Bruce M. Eisen

[57] ABSTRACT

A biocatalytic method for producing a desired amino acid is disclosed. The method involves contacting a 2-ketoacid corresponding to the desired amino acid with lactic acid, aspartic acid and ammonia, or salts thereof, in the presence of:

(a) one or more transaminase enzymes capable of catalyzing the conversion of the 2-ketoacid and L-aspartic acid to the desired amino acid and oxaloacetic acid;

(b) a malate-lactate transhydrogenase enzyme capable of catalyzing the conversion of lactic acid and oxaloacetic acid to pyruvic acid and malic acid;

(c) a fumarase enzyme capable of catalyzing the conversion of malic acid to fumaric acid; and (d) an aspartate-ammonia lyase enzyme capable of catalyzing the conversion of fumaric acid and ammonia to aspartic acid.

10 Claims, No Drawings

PRODUCTION OF AMINO ACIDS USING COUPLED ENZYME SYSTEMS

This invention relates to a method for the production of amino acids in enantiomerically pure form using a biocatalytic system composed of a combination of enzymes, in which the various enzymatic reactions are coupled to produce the final amino acid product. The combination of enzymes includes, generally, one or more transaminases, malate-lactate transhydrogenase, aspartate-ammonia lyase, and fumarase.

BACKGROUND OF THE INVENTION

Amino acids currently have application as additives to animal feed, nutritional supplements for human food, components in infusion solutions, and synthetic intermediates for the manufacture of pharmaceuticals and agricultural chemicals. L-glutamic acid is used as a flavor enhancer for food with a world market of over 1 billion dollars annually. L-lysine and methionine are large volume additives to animal feed, and L-tryptophan and L-threonine have similar potential applications. L-phenylalanine and L-aspartic acid have very important markets as key components in the manufacture of the low-calorie sweetener aspartame, and other promising low-calorie sweeteners have compositions containing certain amino acids as well. Infusion solutions require a range of amino acids including those essential in human diets. D-valine is used in the manufacture of synthetic pyrethroids. D-phenylglycine and derivatives thereof are useful as components of beta-lactam antibiotics. Many other D- and L-amino acids have potential applications as intermediates in the synthesis of pharmaceutically active compounds.

Methods developed for the synthesis of amino acids involve fermentation, chemical synthesis, extraction from protein hydrolyzates, and enzymatic bioconversions. Chemical synthetic methods generally involve the initial formation of a racemic mixture, followed by the resolution of this mixture to yield the optically active product. The resolution may be accomplished either chemically, by fractional crystallization of diasteromeric salts of the amino acid, or if desired, enzymatically using the enzyme L-aminoacylase. In order to make use of the undesired isomer, it must be re-racemized and then recycled through the process. Fermentation methods suffer from problems of slow rates of conversion, costly purifications, and significant capital investments. Extraction from protein hydrolyzates is used only in a few cases because the amino acid of interest is a relatively low percentage of the total protein and purification is therefore generally difficult. Enzymatic conversions offer advantages primarily due to reduced capital investments, lower purification costs, higher rates of conversion, and higher yields.

Although a number of biocatalytic routes have been proposed for the production of L-amino acids, few have been shown to be generally useful for the production of a wide range of different optically active amino acid products. For example, Chibata and co-workers at Tanabe Seiyaku as well as several other companies have developed a process for the production of L-aspartic acid from ammonium fumarate catalyzed by the enzyme aspartase. See Tosa, T. et al., Biotech and Bioeng. 15:69–84 (1973); Wood, L. L. and Carlton, G. J., Bio/technology 2:1081–1084 (1984); and Fusee, M. C. et al., Appl. Environ. Microbiol. 42:672–676 (1981). A process for the production of L-phenylalanine by the phenylalanine ammonia lyase-catalyzed addition of ammonia to trans-cinnamic acid has been developed. See Hamilton, B. K. et al., Trends in Biotechnology 3:64–68 (1985). L-Alanine can be produced by the enzyme-catalyzed decarboxylation of L-aspartic acid (see Fusee, M. C. and Weber, J. E., 1984, Applied and Environmental Microbiology 48:694–698, and references cited therein. However, none of the processes above has been shown to have truly general applicability to the production of a number of different amino acids, both naturally occurring and unnatural.

One previously described enzymatic process which does have general applicability involves the transamination of a given 2-ketoacid to the corresponding L-amino acid (U.S. Pat. No. 4,518,692 (May 1985)). In that process, L-aspartic acid and a 2-ketoacid are reacted in the presence of a transaminase to form the desired L-amino acid and oxaloacetate, followed by decarboxylation of said oxaloacetate to form pyruvate. The essentially irreversible decarboxylation of oxaloacetate drives the entire process to completion to form L-amino acids in yields approaching 100% of theoretical from the corresponding 2-ketoacids. The reaction is summarized in Scheme 1:

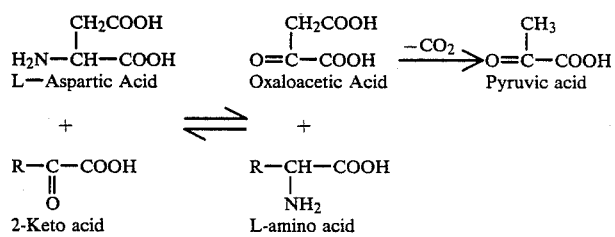

The present invention is an improvement on the processes described in U.S. Pat. Nos. 4,518,692 and 826,766. The present invention provides a method for achieving the advantages of the transamination reaction, but allows the L-aspartic acid to be used in catalytic rather than stoichiometric quantities. L-Aspartic acid is thus replaced as the amino group donor by L-lactic acid, which is produced inexpensively in large quantity by fermentation. By replacing the L-aspartic acid with a less expensive precursor, L-lactic acid, the cost of raw materials for amino acid production is significantly reduced. The present invention affords additional advantages in that the reaction is driven to completion by removal of the oxaloacetate by reduction to L-malic acid rather than by decarboxylation. This eliminates the problems of evolution of gaseous $CO_2$ and the concomitant pH changes associated with the production of $CO_2$ as a byproduct. The present invention is also an improvement over US 4,304,858, DE 3307094, and DE 3307095 which disclose processes involving the reductive amination of 2-ketoacids to form L-amino acids. In the process of the present invention the net reaction catalyzed by the biocatalytic system is a reductive amination of a 2-keto acid with inexpensive L-lactic acid and ammonia to the corresponding optically active amino acid. One advantage of the present invention is that unlike the aforementioned inventions, no nicotinamide cofactors, either unmodified or modified, need be added to the reaction mixture.

SUMMARY OF THE INVENTION

The present invention provides a method for the production of amino acids in pure enantiomeric form from the corresponding 2-ketoacid starting materials catalyzed by a series of coupled enzyme reactions. The method comprises:

Transamination of the 2-ketoacid by aspartic acid using one or more transaminase enzymes, giving rise to the desired amino acid plus oxaloacetate;

Conversion of the oxaloacetate to L-malate in the presence of malate-lactate transhydrogenase and L-lactate;

Conversion of the L-malate to fumarate in the presence of the enzyme fumarase;

Conversion of the fumarate so produced into L-aspartate in the presence of ammonia or a salt thereof and the enzyme aspartate-ammonia lyase, thereby regenerating L-aspartate.

These reactions are described by formulas 1–4 below:

mide cofactors in any form whatsoever. The reaction is driven to completion using an excess of ammonia. By continuously regenerating L-aspartate from oxaloacetate in the presence of L-lactate and ammonia or a salt thereof, L-aspartate may be used in catalytic rather than stoichiometric quantities. L-lactate and ammonia are significantly less expensive than L-aspartate, thus reducing the cost of raw materials for amino acid production. In addition to lowering the cost of production, the removal of oxaloacetate by reduction rather than decarboxylation avoids potential problems with $CO_2$ evolution and pH change.

DETAILED DESCRIPTION OF THE INVENTION

This invention involves a process for the production of amino acids from the corresponding 2-ketoacids using a catalyst consisting of a group of enzymes which catalyze a series of coupled reactions. In the process of the present invention, a 2-ketoacid is transaminated to yield an L-amino acid using L-aspartic acid as the amino group donor. That transamination reaction also yields oxaloacetate as a byproduct. This reaction, which normally has an equilibrium constant near unity, is driven to completion by removal of the oxaloacetate as it is formed. This removal of oxaloacetate is accomplished by an enzyme-catalyzed reduction of the oxaloacetate to L-malate by hydride transfer from L-lactate. The L-malate formed as a product of this reaction is dehy-

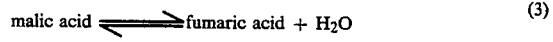

The net overall reaction described by formulas 1–4 is as follows:

The coupled nature of these enzyme-catalyzed reactions is depicted schematically as follows:

drated to fumarate in a reaction catalyzed by the enzyme fumarase; finally, the fumarate is reacted with ammonia in the presence of the enzyme aspartase to form L-aspartate, thus regenerating an amino group

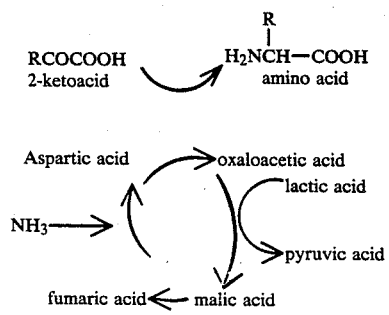

The enzymatic reactions are coupled in such a way that, overall, the net reaction is the reductive amination of a given 2-ketoacid to the corresponding amino acid by reaction with L-lactate and ammonia, but without the requirement for the separate addition of nicotinadonor for another transamination reaction. The net reaction catalyzed by the multi-enzyme system is the reductive amination of a 2-ketoacid to an enantiomerically pure amino acid using ammonia and L-lactic acid.

One significant advantage of this biocatalytic system is that this reductive amination is carried out without the need for the separate addition of nicotinamide cofactor in any form.

A schematic diagram of the process is shown previously under "Summary of the Invention".

The reaction sequence is initiated by the transamination of a 2-ketoacid with L-aspartic acid to produce the desired amino acid and the byproduct oxaloacetate. There are a number of advantages associated with the transamination reaction. These are described below:

1. The desired optically pure amino acids are produced stereoselectively. The undesired optical isomer is not produced and no optical resolution is required.
2. .The 2-keto acid precursors are conveniently available from chemical synthesis or may be produced in situ from conveniently available corresponding amino acids.
3. The rates of reaction are relatively rapid.
4. The capital costs are lower than for a fermentation process.
5. The technology is general because transaminases with varying selectivities are known, e.g. aromatic amino acid transaminases, branched chain amino acid transaminases, transasminases specific for amino acids having acidic side chains, etc.
6. The 2-ketoacid co-product pyruvate is easily isolated and may also have significant value, further enhancing the overall economics of the process.

In an earlier patent (U.S. Pat. No. 4,518,692) a method was described for driving such processes to completion by the essentially irreversible decarboxylation of the oxaloacetate to pyruvate. Removal of oxaloacetate as it is formed in effect drives the entire process to completion. Using the method just described, amino acids can be produced from the corresponding 2-ketoacids in yields approaching 100% of theoretical. This approach was further improved upon in U.S. Pat. No. 4,826,766. That application describes a method for achieving the advantages of using L-aspartic acid as the amino donor in a two-stage transamination process, even when the desired transaminase enzyme utilizes L-aspartic acid either poorly or not at all as a direct transaminating agent.

The present invention is a further improvement over both of the prior inventions. One of the advantages of the present invention is that the L-aspartic acid is continuously regenerated in situ, thereby being required only in catalytic quantities rather than in stoichiometric quantities. Since the regenerating agents, L-lactate and ammonia, are significantly less expensive than L-aspartic acid, the cost of raw materials for amino acid production is reduced. Another advantage of the present invention is that the oxaloacetate byproduct, which is a competitive inhibitor of many transaminases, is removed by transhydrogenation with lactate rather than by decarboxylation. The $K_m$ for oxaloacetate with malate-lactate transhydrogenase is $50 \times 10^{-6}M$, compared to $2-3 \times 10^{-3}M$ for oxaloacetate decarboxylase; thus, malate-lactate transhydrogenase operates efficiently to remove oxaloacetate at concentrations almost two orders of magnitude lower than the decarboxylase, and thus is a more effective scavenger of oxaloacetate. The transhydrogenase catalyzed reaction is also much faster than the nonenzymatic decarboxylation of oxaloacetate. The transhydrogenation reaction is further distinguished from the decarboxylation reaction, whether enzymatic or non-enzymatic, in that no metal ions are required for the reaction. Yet another advantage of the transhydrogenase reaction over the decarboxylation is that no $CO_2$ is evolved in the process; thus there are no problems associated with the evolution of gas, the accumulation of high concentrations of bicarbonate, or changes in the pH of the reaction solution The present invention is also an improvement over U.S. Pat. Nos. 4,326,031; 4,304,858; DE Nos. 3307094; 3307095 and EP application No. 040281. In the processes described in those patents and patent applications, an enzyme system is used to reductively aminate a 2-ketoacid to an L-amino acid in the presence of ammonia, a nicotinamide cofactor, and an external cofactor recycling system such as formate dehydrogenase and formate. In such processes, the nicotinamide cofactor is added in excess, and in some embodiments is chemically modified with a water soluble polymer such as polyethylene glycol or dextran.

In the process of the present invention the net reaction catalyzed by the biocatalytic system is a reductive amination of a 2-keto acid with lactic acid and ammonia to the corresponding optically active amino acid. A significant advantage of the biocatalytic system of the present invention is that no nicotinamide cofactors, either unmodified or modified, need be added to the reaction mixture, nor is an external cofactor recycling system necessary.

In accordance with this invention, the transaminase (aminotransferase E.C. 2.6.1.) enzymes may be chosen from any available source. Some transaminase enzymes useful in the practice of this invention are described by E. Umbarger in *Annual Rev. Biochem.*, Vol. 117, pp. 533–606 (1978) and in *Amino Acids: Biosynthesis and Genetic Regulation*, K. M. Merrman and R. L. Somerville, eds., pp. 19–34 (Addison-Wesley, 1983).

Such transaminases can be prepared from the following microorganisms, for example, by methods known in the art: *Escherichia coli* (*E. coli*), *Bacillus subtilis*, *Bacillus stearothermophilus*, *Archaromobacter eurydice*, *Klebsiella aerogenes*, *Saccharomyces cerevisiae*, *Pseudomonas putida*, and the like. Some other transaminases useful in the practice of this invention are listed in Enzyme Nomenclature, pp. 220–230 (Academic Press, 1984).

Also, in accord with this invention, the malate-lactate transhydrogenase enzyme (lactate-malate transhydrogenase; E. C. 1.1.99.7) has been shown to exist in certain anaerobic bacteria of the genus Veillonella (renamed from Micrococcus lactyliticus) from which it may be recovered and/or purified Other sources of the same or similar enzymatic activity may also produce suitable enzymes for use in the present invention. This enzyme is described in the following references, which together with the references contained therein are hereby incorporated by reference:

1. S. H. George Allen, *Methods in Enzymology* Vol. 89, 367–376 (1982);
2. M. I. Dolen, *Journal of Biol. Chem.*, Vol. 244, 5273–5285 (1969);
3. S. M. George Allen and Jaygonda R. Patil, *J. Biol. Chem.*, Vol. 247, 909–916 (1972);
4. S. M. George Allen, *Eur. J. Biochem.*, Vol. 35, 338–345 (1973);
5. M. I. Dolen, E. F. Phares, and M. V. Long, *Biochem. Biophys. Res. Comm.*, Vol 21, 303–310 (1965);
6. S. M.George Allen, *J. Biol. Chem.*, Vol. 241, 5266–5275 (1966).

In accord with the practice of this invention, the enzymes aspartase (aspartate-ammonia lyase; E. C.

4.3.1.1) and fumarase (S-malate hydro-lyase; E. C. 4.2.1.2) are widely distributed in nature, and the enzymes from any animal, plant or microbial source may be used. These enzymes and conventional methods for recovery and/or purification of such enzymes have been described in the literature; representative references may be obtained from Enzyme Nomenclature (Academic Press, 1984) or from the series Methods in Enzymology.

The process of this invention can be used for the production of a large variety of L-amino acids by choosing the appropriate 2-ketoacid precursor and a transaminase enzyme r enzymes (cf U.S. Pat. No. 4,826,766) capable of transaminating it with L-aspartic acid. For example, L-phenylalanine was prepared in high yield by the process of the present invention from phenylpyruvate, L-lactate, and $NH_3$ in the presence of catalytic amounts of L-aspartic acid and the enzymes aspartic transaminase from *E. coli* (aspC gene product), malate-lactate transhydrogenase from *Veillonella alcalscens*, aspartase from *E. coli*, and fumarase from porcine heart. Using the same set of enzymes as the biocatalytic system, p-hydroxyphenylpyruvic acid can be converted into L-tyrosine, indole-3-pyruvate can be converted into L-tryptophan, 2-ketoglutarate can be converted into L-glutamic acid, 2-oxo-4-thiomethylbutanoic acid can be converted into L-methionine, 2-oxo-4-phenylbutanoic acid can be converted into 4-phenyl-2-aminobutanoic acid, 2-ketoadipic acid can be converted into L-2-aminoadipic acid, and many other similar 2-ketoacids may be converted into their corresponding L-amino acids. Using transaminases with the appropriate specificities, any other L-amino acids, either naturally occurring or unnatural may be prepared.

In cases where L-aspartic acid functions either poorly or not at all as a direct amino group donor with the transaminase of the desired specificity, this invention can be used in conjunction with the indirect transamination method of U.S. Pat. No. 4,826,766 which is hereby incorporated by reference. That method involves the use of a first transaminase enzyme to catalyze an amino group transfer from a first amino acid, here aspartic acid, to a first keto acid and thence to a second keto acid to yield the desired amino acid. The amino group transfer to the second keto acid (the precursor for the desired amino acid) is catalyzed by a second transaminase enzyme with the desired specificity for the transamination reaction producing the desired amino acid. The use of a second keto acid and transaminase enzyme is advantageous, as mentioned above, in cases where aspartic acid functions poorly or not at all as a direct transaminase-catalyzed amino group donor to the keto acid precursor of the desired amino acid. L-aspartic acid is still used in only catalytic quantities, and is regenerated in situ. Exemplary conversions carried out in accordance with this embodiment using aspartase and the asp C and ilvE transaminases from *E. coli*, fumarase from porcine heart and malate-lactate transhydrogenase from *Veillonella alcalescens* include the conversion of 2-ketoisocaproic acid into L-leucine, 2-ketoisovaleric acid into L-valine and 3-methyl-2-ketovaleric acid into L-isoleucine.

In all embodiments, the 2-ketoacid starting material may be described by the general structural formula R—CO—COOH, in which R can be selected from a wide variety of substituents, for example, hydrogen, substituted and unsubstituted lower alkyl, substituted and unsubstituted lower aryl, and heterocyclic groups.

The term "lower alkyl" as used herein means both straight chain and branched chain alkyl groups having from one to about 10 carbon atoms. "Substituted lower alkyl" groups means lower alkyl groups substituted at any location with hydroxy, alkoxy, mercapto, carbamoyl, fluoro, chloro, bromo, iodo, amino, amidino, and R'-thio (where R' is lower alkyl or substituted lower alkyl or lower aryl or substituted lower aryl) groups. These groups include those found in natural amino acids as well as unnaturally occurring amino acids.

The term "lower aryl" as used herein means phenyl, benzyl, phenylethyl, phenylpropyl, and other homologous groups. "Substituted lower aryl" groups include phenyl, benzyl, phenylethyl, phenylpropyl, and other homologous groups substituted with the same groups as those listed above for lower alkyl.

Heterocyclic groups as used herein means 4-imidazoylmethyl, 3-indoylmethyl, 2-furanoylmethyl, 2-pyrazoylnethyl, groups homologous to those, and other similar heterocyclic groups.

The enzymatic reactions of this invention may be carried out at temperatures ranging from about 4° C. to about 80° C., most preferably from about 20° C. to about 65° C. The optimal pH for the reactions ranges from about 2.0 to about 12.0, most preferably from about 4.0 to about 9.5. The small molecule pyridoxal phosphate is preferably used as a cofactor for the transaminase enzyme or enzymes, and may be added at a concentration of about 0.01 millimolar to about 1.0 millimolar.

The enzymes used in this invention can be added to the reaction mixture in whole cells, crude cell lysates, as partially purified enzyme or purified enzyme. The enzymes can be purified if desired by techniques well known to those skilled in the art.

The enzymes can be used in solution or as immobilized enzymes, as aforesaid, in the practice of this invention.

Immobilization methods which may be used in the practice of this invention include entrapment in polymeric gels, covalent attachment, crosslinking, adsorption and encapsulation as is known in the art, see e.g., A. M. Klibanov, Science 219: 722–727 (1983) and references therein and in Methods in Enzymology 44 (K. Mosbach, ed.). One example of an immobilized enzyme system is described by Weetall et al., Methods in Enzymology 34, pp. 59–72 (1974), which is hereby incorporated by reference. Weetall et al. describe a method for immobilizing enzymes on glutaraldehyde activated controlled pore glass beads (Corning).

In accord with this method, transaminases may be coupled to the glass particles by reacting the enzymes with the activated glass particles at 0°–5° C.. for 2 hours in a phosphate buffer solution having a pH of 7.0. The coupled enzymes can be used directly or first reacted with 1% sodium borohydride to stabilize the covalent link between the enzyme and the activated glass.

In another embodiment, alumina or silica particles are first impregnated with polyethyleneimine, followed by activation with glutaraldehyde. The enzyme is then covalently attached to the activated support.

Other suitable sustrates for immobilizing enzymes for the practice of this invention include porous ceramic, porous silica, bentonite, diatomaceous earth, sepharose, cellulose and cellulose derivates, polyacrylamide, polyazetidine, carrageenan, chromosorb and the like. These substances can be activated, if desired, by techniques well known in the art.

The reaction may also be carried out in continuous flow mode by packing the immobilized enzymes into a bioreactor. Numerous configurations for such bioreactors are known in the art.

By choosing appropriate transaminase enzymes, either D- or L-amino acids may be specifically produced by the method of this invention. For example, where D-amino acids are desired, one would typically utilize D-transaminases, which are specific for D-amino acids. A number of D-transaminases have been isolated which will catalyze the synthesis of D-amino acids. See *Biochemical and Biophysical Research Communications*, 122:485–491 (1984); Yonaha, K., et al, *Amino Acid, Nucl. Acid* (Japan), 32:34–35 (1975); Soper, T. S. and Manning, J. M., *J. Biol. Chem.*, 256:a4263–4268 (1981); and Soper, T. S., et al., *J. Biol. Chem.*, 252:1571–1575 (1978) which are incorporated herein by reference. These and any other transaminases which will result in the formation of a D-amino acid can readily be utilized in the process described herein. In this particular embodiment, the L-aspartic acid is racemized in situ, either chemically or enzymatically, to the D-enantiomer in order to function as a donor for the D-transaminase.

The process of the present invention is equally applicable to the production of amino acids, either D or L, containing one or more stable or radioactive isotopes such as $^{14}C$, $^{13}C$, $^{2}H$, $^{3}H$, $^{17}O$, $^{18}O$ or $^{15}N$ simply by using an appropriately isotopically labeled ketoacid, L-aspartic acid, ammonia or water solvent.

The enantiomerically pure amino acid products may be recovered by any method known in the art, for example crystallization, solvent precipitations, ion exchange separations, and the like. Such separations also allow the recovery of the pyruvate acid co-product.

The invention will now be further illustrated by the following examples which are presented for illustrative purposes only and are not intended to, and should not be construed to, limit the scope of the invention as described in the claims which follow thereafter.

EXAMPLES

Example 1: Preparation of L-Phenylalanine

To demonstrate that L-amino acids can be produced efficiently using catalytic quantities of L-aspartic acid, a solution was prepared with the following composition:
  50 mM potassium phosphate, pH 7.5
  50 mM L-lactate
  50 mM phenylpyruvate
  50 mM ammonium chloride
  1 mM magnesium chloride
  10 mM L-aspartate
  0.1 mM pyridoxal phosphate
Four parallel reactions were carried out using this solution to which had been added:
  1. Complete catalytic system consisting of 5 International Units of aspC transaminase from *E. coli*, 5 Int. Units of malate-lactate transhydrogenase from Veillonella alcalescens, 0.2 Int. Units of aspartase from *E. coli*, and 17.5 Int. Units of fumarase from porcine heart
  2. Complete system without the aspC transaminase
  3. Complete system without the malate-lactate transhydrogenase
  4. Complete system without L-lactate.
The results shown in the table below indicate that only the complete catalytic system is capable of producing L-phenylalanine beyond the 10 mM level (20% conversion) of L-aspartic acid in the reaction mixture, and therefore that the recycle system is successful only when the complete catalytic system is used.

| | % Conversion of Phenylpyruvate to L-Phenylalanine | | | |
| --- | --- | --- | --- | --- |
| | Time (min) | | | |
| Reaction | 0 | 85 | 180 | 600 |
| 1 | 0% | 14% | 17.5% | 38.5% |
| 2 | 0% | 0.4% | 0% | — |
| 3 | 0% | 2.5% | — | 16.5% |
| 4 | 0% | 3% | 3% | 11.3% |

EXAMPLE 2

This reaction was carried out as in Example 1 except that the following concentrations were used:
25 mM phenylpyruvate, 25 mM L-lactate, 25 mM ammonium chloride, 5 mM L-aspartic acid, 0.1 mM pyridoxal phosphate, and 25 mM ammonium chloride. The production of L-phenylalanine was monitored over time and the results are shown in the table below.

| % Conversion of Phenylpyruvate to L-Phenylalanine | |
| --- | --- |
| Time (Min) | % conversion |
| 0 | 0 |
| 30 | 29 |
| 600 | 74 |

What is claimed is:

1. A biocatalytic method for producing a desired amino acid which comprises contacting a 2-ketoacid corresponding to the desired amino acid with lactic acid, aspartic acid and ammonia, or salts thereof, in the presence of:
  (a) one or more transaminase enzymes capable of catalyzing the conversion of the 2-ketoacid and L-aspartic to the desired amino acid and oxaloacetic acid;
  (b) a malate-lactate transhydrogenase enzyme capable of catalyzing the conversion of lactic acid and oxaloacetic acid to pyruvic acid and malic acid;
  (c) a fumarase enzyme capable of catalyzing the conversion of malic acid to fumaric acid; and
  (d) an aspartate-ammonia lyase enzyme capable of catalyzing the conversion of fumaric acid and ammonia to aspartic acid;
said contacting being under suitable conditions permitting the production of the desired amino acid.

2. The method of claim 1 which further comprises recovering the desired amino acid from the other acids, enzymes and ammonia.

3. The method of claim 1, wherein the enzymes are purified or partially purified enzyme preparations, or are contained in whole cells.

4. The method of claim 3, wherein each enzyme is immobilized on an insoluble support.

5. The method of claim 4, wherein the insoluble support is a controlled pore ceramic particle or controlled pore glass particle.

6. The method of claim 4, wherein the enzymes are immobilized on the same support.

7. The method of claim 4, wherein the enzymes are immobilized on a polyethyleneimine treated particle.

8. The method of claim 1, wherein the desired amino acid is an L-amino acid or a D-amino acid, respectively, and is substantially enantiomerically pure.

9. The method of claim 1, wherein the desired amino acid is isotopically labeled.
10. The method of claim 1, wherein the desired amino acid is of formula
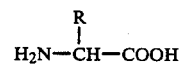
wherein R is —H; substituted or unsubstituted lower alkyl or aryl; or heterocyclic.
* * * * *